United States Patent [19]

Gschwend

[11] 3,947,585
[45] Mar. 30, 1976

[54] PYRAZOLOBENZAZEPINES

[75] Inventor: Heinz Werner Gschwend, New Providence, N.J.

[73] Assignee: Ciba-Geigy Corporation, Ardsley, N.Y.

[22] Filed: June 3, 1974

[21] Appl. No.: 475,474

[52] U.S. Cl. ............... 424/273; 424/246; 424/248; 424/250; 424/263; 424/267
[51] Int. Cl.² ...... A61K 31/415; A61K 31/54; A61K 31/535; A61K 31/445
[58] Field of Search ......... 260/310 R; 424/273, 248, 424/246, 250, 263, 267

Primary Examiner—Donald B. Moyer
Attorney, Agent, or Firm—Joseph G. Kolodny; Theodore O. Groeger; John J. Maitner

[57] ABSTRACT

6-Aryl-1 or 2H,4H-pyrazolo[4,3-d](2)-benzazepines, e.g. those of the formula

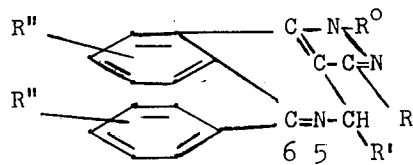

R = H or alkyl
R° = H, alkyl, (HO, alkoxy, amino)-alkyl, aralkyl or aryl
R' = H, OH or alkyl
R" = H, alkyl, alkoxy, halo or $CF_3$ 5,6-dihydro- or 5-alkyl-5,6-dihydro-derivatives, N-oxides, acyl derivatives or therapeutically useful acid addition salts thereof exhibit antianxiety and antidepressant effects.

3 Claims, No Drawings

PYRAZOLOBENZAZEPINES

SUMMARY OF THE INVENTION

The present invention concerns and has for its object the provision of new 6-aryl-1 or 2H,4H-pyrazolo[4,3-d](2) benzazepines, preferably of those corresponding to the tautomers of Formulae I and II

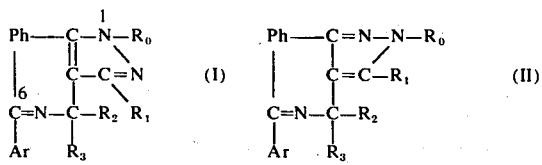

wherein Ph is a 1,2-phenylene radical, Ar is a monocyclic, carbo-cyclic aryl radical, $R_o$ is hydrogen, lower alkyl, (hydroxy, lower alkoxy or Am)- $C_mH_{2m}$ or Ar-$C_nH_{2n}$, wherein Am is an open or cyclic amino group, $m$ is an integer from 1 to 7, $n$ such from 0 to 7, each of $R_1$, and $R_2$ is hydrogen or lower alkyl and $R_3$ is hydrogen, lower alkyl, hydroxy or lower alkanoyloxy; or a 5,6-dihydro- or 5-lower alkyl-5,6-dihydro-derivative; an N-oxide of the compounds containing no hydrogen attached to nitrogen; or a lower alkanoyl, alkoxycarbonyl, AmCO, AmCS or cyano derivative of the compounds containing at least one hydrogen attached to nitrogen; or therapeutically useful acid addition salts thereof; as well as of corresponding pharmaceutical compositions and of methods for the preparation and application of these products, which are useful antianxiety and antidepressant agents.

DESCRIPTION OF THE PREFERRED EMBODIMENTS

The 1,2-phenylene radical Ph, as well as the aryl radical Ar, are unsubstituted or substituted by one or more than one, preferably by one or two, of the same or different substituents selected from the group consisting of lower alkyl, e.g. methyl, ethyl, n- or i-propyl or -butyl; etherified or esterified hydroxy, such as lower alkoxy, e.g. methoxy, ethoxy, n- or i-propoxy or -butoxy; or halo, e.g. fluoro, chloro or bromo; or trifluoromethyl. The term "lower", referred to above and hereinafter in connection with organic radicals or compounds respectively, defines such with up to 7, preferably up to 4, carbon atoms.

Preferred 1,2-phenylene radicals Ph are 1,2-phenylene, (lower alkyl)-1,2-phenylene, (lower alkoxy)-1,2-phenylene, (halo)-1,2-phenylene or (trifluoromethyl)-1,2-phenylene and preferred aryl radicals Ar are phenyl, (lower alkyl)-phenyl, (lower alkoxy)-phenyl, mono- or di-(halo)-phenyl or (trifluoromethyl)-phenyl.

The radical $R_o$ preferably represents hydrogen, lower alkyl or Ar-$C_nH_{2n}$, wherein $n$ is an integer from 0 to 7, preferably 1 to 4. It may also represent (hydroxy, lower alkoxy or Am)-$C_mH_{2m}$ wherein $m$ is an integer from 1 to 7 and Am is exemplified by amino, mono- or di-lower alkylamino, lower alkyleneimino or mono-aza-, oxa- or thiaalkyleneimino, wherein the additional nitrogen, oxygen or sulfur atom is separated from the iminonitrogen by at least 2 carbon atoms, e.g. mono- or di-(methyl, ethyl, n- or i-propyl or -butyl)-amino; pyrrolidino, piperidino or hexamethyleneimino; piperazino, 4-(lower alkyl, e.g. methyl or ethyl)-piperazino; morpholino or thiamorpholino. Preferred amino groups Am are mono- or di-lower alkylamino, pyrrolidino, piperidino, piperazino, 4-(lower alkyl)-piperazino or morpholino.

The radicals $R_1$, $R_2$ and $R_3$ represent preferably a hydrogen atom, but also lower alkyl, above all methyl and $R_3$ also hydroxy or lower alkanoyloxy, e.g. acetoxy, propionyloxy or pivalyloxy.

The N-oxide is preferably the 5-N-oxide and the acyl derivatives are either derived from the compounds containing a primary or secondary Am, or from the tautomers of Formula II, wherein $R_0$ is H. Lower alkanoyl derivatives are examplified by formyl, acetyl, propionyl or pivalyl derivatives, lower alkoxycarbonyl derivatives by methoxy-, ethoxy-, n- or i-propoxy- or -butoxy-carbonyl derivatives and AmCO or AmCS by the above examples.

The compounds of the invention exhibit valuable pharmacological properties, for example, imipramine-type antidepressant and especially antianxiety effects of long duration. This can be demonstrated in animal test, using advantageously mammals, such as mice, rats or monkeys, as test objects. The compounds of the invention can be applied to the animals enterally, e.g. orally, or parenterally, such as subcutaneously or intraperitoneally, e.g. in the form of aqueous solutions or starchy suspensions. The dosage may range between about 0.1 and 300 mg/kg/day, preferably between about 1 and 100 mg/kg/day, advantageously between about 2 and 20 mg/kg/day. An antidepressant effect is observed, for example, in the amphetamine interaction test (P. Carlton, Psychopharmacologia 1961, Vol II, p. 364) performed with male albino rats, which are trained to press a bar every 30 seconds, in order to avoid an electric shock applied through the floor grid. In case the animals receive i.p. 0.25 mg/kg/day of amphetamine, their performing rate for avoiding said shocks during a test period or about 4–5 hours is slightly higher than that of placebo (saline) treated animals. In case the animals receive the compounds of the invention (or imipramine for control purposes) in the above-mentioned doses, preferably at 5 or 10 mg/kg/day i.p. and about 45 minutes later the amphetamine, their rate of avoiding the shocks is highest, as compared with that of rats receiving (a) saline alone, (b) saline and amphetamine, or (c) the compounds of the invention and saline. Primarily, however, the compounds of the invention exhibit antianxiety effects in rats or squirrel monkeys, advantageously at dosages between about 2 and 20 mg/kg/day. Accordingly, they reduce acquired fear or anxiety associated with a psychological conflict. It is established by simultaneously rewarding with food and punishing with electric shock all lever-pressing responses of the animals made in the presence of a discriminative tone stimulus. For example, rats first learn to press a lever to obtain milk reward, which is delivered on the average of once per two minutes. After this schedule, which lasts 15 minutes, a tone stimulus of three minute duration is presented. This stimulus signals a change from a variable interval schedule of reinforcement, to a continuous reinforcement schedule (CRF). During the CRF schedule, all lever responses not only produce milk rewards but also an electric shock to the animals'feet. During the period in which a shock accompanies the food reward, the tone stimulus produces a suppression of all lever pressing responses. Thus, for example, administration of 8-chloro-6- (2-fluorophenyl)-1-methyl-1H,4H-pyrazolo[4,3-d](2)benzazepine or salts thereof, a characteristic compound of the invention, appplied at about 5 mg/kg/day intraperitoneally to rats or orally to squirrel monkeys, reinstate these responses, indicating that the animals tolerate more shocks in obtaining the food reinforcement. Accordingly, the compounds of the invention are useful antidepressants and in combatting anxiety problems. Moreover, they are also valuable intermediates in the preparation of other useful products, especially of pharmacologically active compounds.

Particularly useful are compounds of Formulae I and II, in which Ph is 1,2-phenylene, (lower alkyl)-1,2-phenylene, (lower alkoxy)-1,2-phenylene, (halo)-1,2-phenylene or (trifluoromethyl)-1,2-phenylene, Ar is H-Ph, $R_o$ is hydrogen, lower alkyl, (hydroxy, lower alkoxy or Am)-$C_mH_{2m}$, or Ar-$C_nH_{2n}$, wherein Am is amino, mono- or di-lower alkylamino, or five to seven ring-membered lower alkylenemino, $m$ is an integer from 2 to 4, and $n$ such from 0 to 4, each of $R_1$ and $R_2$ is hydrogen or lower alkyl, and $R_3$ is hydrogen, lower alkyl, hydroxy or lower alkanoyloxy, an N-oxide of the compounds containing no hydrogen attached to nitrogen, or a lower alkanoyl, alkoxycarbonyl, AmCO or AmCS derivative of the compounds containing at least one hydrogen attached to nitrogen, or a therapeutically useful acid addition salt thereof.

Preferred compounds of the invention are those of Formulae I and II, wherein Ph is 1,2-phenylene, (alkyl)-1,2-phenylene or (halo)-1,2-phenylene, Ar is H-Ph, $R_o$ is hydrogen, alkyl, 2- or 3-(hydroxy or dialkylamino)-(ethyl or propyl) or H-Ph-methyl, each of $R_1$ and $R_2$ is hydrogen or methyl, and $R_3$ is hydrogen or hydroxy, the 5-N-oxide, an alkanoyl, alkoxycarbonyl, mono- or dialkylcarbamoyl or -thiocarbamoyl derivative of the compounds of Formula II wherein $R_o$ is H, and in which compounds alkyl, alkanoyl or alkoxy has up to 4 carbon atoms, or a therapeutically useful acid addition salt thereof.

Outstanding are the compounds of Formulae III and IV

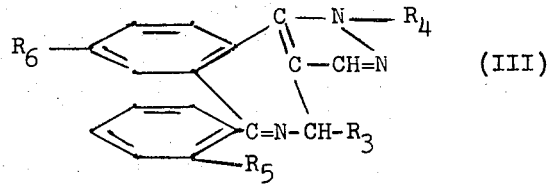

(III)

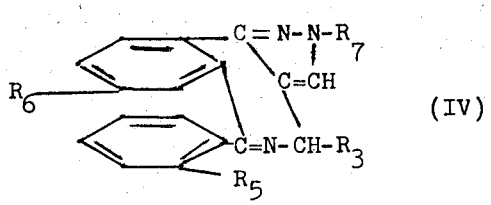

(IV)

wherein $R_3$ is hydrogen or hydroxy, $R_4$ is hydrogen, methyl, ethyl, n- or i-propyl,n-, i- or t-butyl, 2- or 3-(hydroxy, dimethylamino- or diethylamino)-(ethyl or propyl) or benzyl, each of $R_5$ and $R_6$ is hydrogen, methyl, fluoro or chloro and $R_7$ is $R_4$ or formyl, acetyl, (methoxy or ethoxy)-carbonyl, mono- or dimethyl or -ethylcarbamoyl or -thiocarbamoyl, or a therapeutically acceptable acid addition salt thereof.

The compounds of this invention are prepared according to conventional methods, for example by dehydrating compounds of Formula V

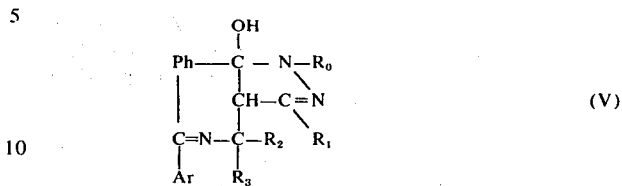

(V)

and, if desired, converting any resulting product into another compound of the invention.

Dehydration is advantageously performed by pyrolytic action at moderately raised temperatures, e.g. in the range between room temperature and the melting point of the starting material, preferably between about 50° and about 150°.

Dehydration is easier achieved with the use of acidic agents, advantageously mineral acids, such as hydrohalic, sulfuric or phosphoric acids, either in single- or multi-phasic media, e.g. aqueous media for said acids and water-immiscible organic solvents for the starting material.

Another process for the preparation of compounds of Formulae I and II consists in condensing compounds of Formulae Va or Vb

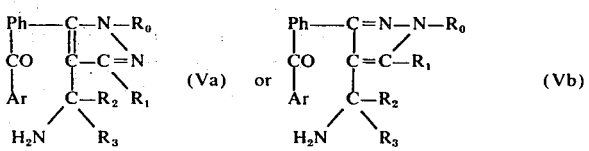

(Va)    or    (Vb)

and, if desired converting any resulting product into another compound of the invention.

Said condensation is preferably performed under neutral or mildly basic conditions, for example in said water-immiscible organic solvents for the starting material Va or Vb and in the presence or absence of ammonia or other nitrogen bases, such as pyridine, mono-, di- or tri-lower alkylamines or -pyridines, at room temperature or up to about 100°.

The 5,6-dihydro-derivatives of compounds I or II are obtained according to acidic reduction methods, for example with nascent or catalytically activated hydrogen, e.g. electrolytically generated hydrogen or molecular hydrogen in the presence of catalysts, such as palladium, or with reduction agents, such as complex borohydrides, e.g. sodium cyanoborohydride, at a pH at or lower than 6, for example in the presence of mineral or carboxylic acids, e.g. hydrochloric or acetic acid.

The compounds thus obtained can be converted into each other according to conventional methods. For example, resulting compounds containing at least one hydrogen atom attached to oxygen or nitrogen can be acylated, for example, with the use of reactive functional derivatives of the corresponding acids, such as halides or anhydrides thereof, e.g. acetyl or propionyl chloride, lower alkyl chloroformates, carbamoyl or thiocarbamoyl chlorides; acetic anhydride, ketene, isocyanates or isothiocyanates. Said primary or secondary amines can also be reacted with reactive esters of the respective alcohols, preferably derived from hydrohalic, aliphatic or aromatic sulfonic acids, e.g. lower alkyl or aralkyl chlorides, bromides, iodides; alkane- or benzenesulfonates, e.g. the mesylate or tosylate, or with corresponding aldehydes or ketones and reducing agents, e.g. formic acid, in order to obtain sec. or tert. amines respectively. Resulting tert. amines can also be converted into 2-N-oxides, for example, by treating them with oxidation agents, such as hydrogen peroxide, aliphatic or aromatic percarboxylic acids, e.g. peracetic or perbenzoic acid. Finally, a resulting base can be converted into a corresponding acid addition salt, preferably with the use of a terapeutically useful acid or anion exchange preparation, or resulting salts can be converted into the corresponding free bases, for example, with the use of a base, such as a metal hydroxide, basic salt, ammonia, amine or cation exchange preparation, e.g. an alkali metal hydroxide or carbonate. Said acid addition salts are preferably such of therapeutically useful inorganic acids, such as strong metalloidic acids, for example hydrohalic, e.g. hydrochloric or hydrobromic acid; sulfuric, phosphoric, nitric or perchloric acid; aliphatic or aromatic carboxylic or sulfonic acids, e.g. formic, acetic, propionic, succinic, glycollic, lactic, malic, tartaric, citric, ascorbic, maleic, hydroxymaleic, pyruvic phenylacetic, benzoic, 4-aminobenzoic, anthranilic, 4-hydroxybenzoic, salicylic, 4-aminosalicyclic, embonic, nicotinic; methanesulfonic, ethanesulfonic, hydroxyethanesulfonic, ethylenesulfonic, halogen-benzenesulfonic, toluenesulfonic, naphthalenesulfonic, sulfanilic or cyclohexylsulfonic acid.

These or other salts, for example, the picrates, can also be used for purification of the bases obtained; the bases are converted into salts, the salts are separated and the bases are liberated from the salts. In view of the close relationship between the free compounds and the compounds in the form of their salts whenever a compound is referred to in this context, a corresponding salt is also intended, provided such is possible or appropriate under the circumstances. Resulting mixtures of isomers can be separated into the single isomers by methods in themselves known, e.g. by fractional distillation, crystallization and/or chromatography.

The invention further includes any variant of the present process in which an intermediate product obtainable at any stage of the process is used as starting material and any remaining steps are carried out, or the process is discontinued at any stage thereof, or in which the starting materials are formed under the reaction conditions, or in which the reaction components are used in the form of their salts. Mainly those starting materials should be used in the reactions of the invention that lead to the formation of those compounds indicated above as being especially valuable.

The starting material is new and considered as additional subject matter of the present invention. It is prepared according to the following formula scheme, which is illustrated by the examples herein:

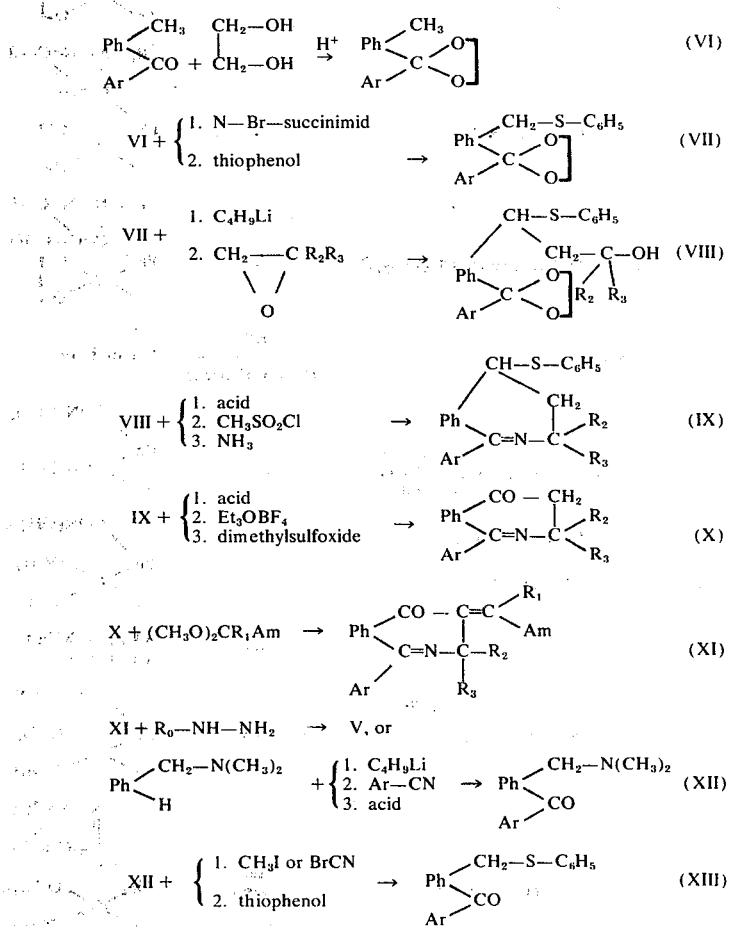

Compounds of Formula XI exhibit the same or similar antianxiety and antidepressant effects as those of I and II.
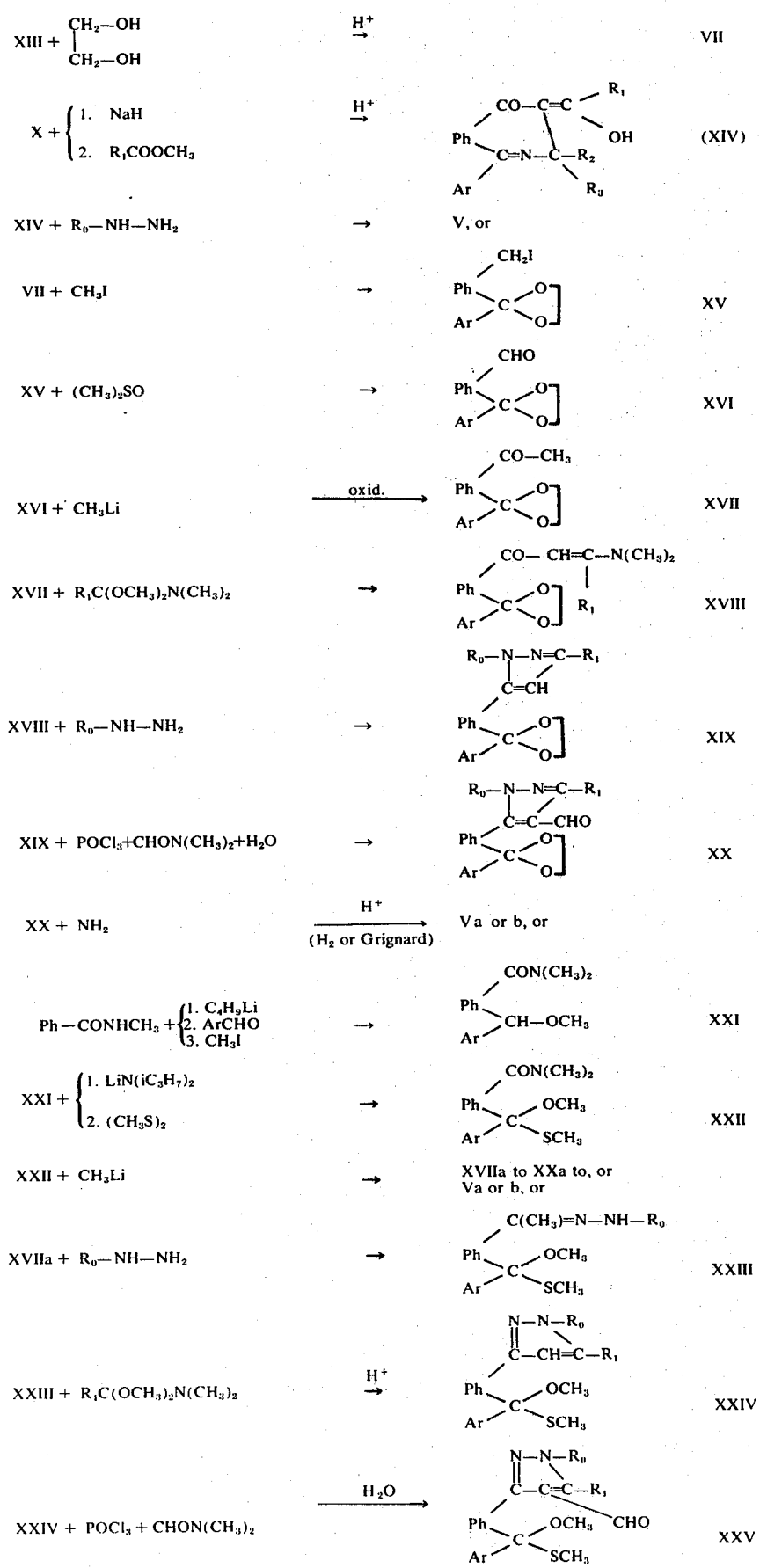

XXV + NH₂OCH₃ → Va, or

XXII + CH₂=CHMgBr →

XXVI + R₁C(OCH₃)₂N(CH₃)₂ →

XXVII + R₀—NH—NH₂ →

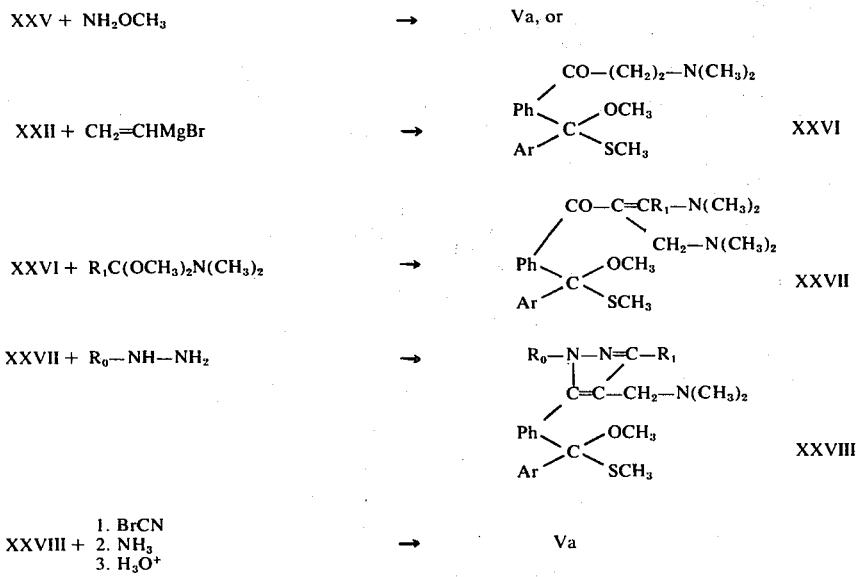

XXVIII + 1. BrCN
2. NH₃   → Va
3. H₃O⁺

The pharmacologically active compounds of the invention are useful in the manufacture of pharmaceutical compositions containing an effective amount thereof in conjunction or admixture with excipients suitable for either enteral or parenteral application. Preferred are tablets and gelatin capsules comprising the active ingredient together with (a) diluents, e.g. lactose, dextrose, sucrose, mannitol, sorbitol, cellulose and/or glycine, (b) lubricants, e.g. silica, talcum, stearic acid, its magnesium or calcium salt and/or polyethyleneglycol, for tablets also (c) binders, e.g. magnesium aluminum silicate, starch paste, gelatin, tragacanth, methylcellulose, sodium carboxymethylcellulose and/or polyvinylpyrrolidone, if desired, (d) disintegrants, e.g. starches, agar, alginic acid or its sodium salt, enzymes of the binders or effervescent mixtures and/or (e) absorbents, colorants, flavors and sweeteners. Injectable compositions are preferably aqueous isotonic solutions or suspensions, and suppositories are advantageously fatty emulsions or suspensions. They may be sterilized and/or contain adjuvants, such as preserving, stabilizing, wetting or emulsifying agents, solution promoters, salts for regulating the osmotic pressure and/or buffers. They may also contain other therapeutically valuable substances. Said pharmaceutical compositions are prepared according to conventional mixing, granulating or coating methods respectively and contain about 0.1 to 75%, preferably about 1 to 50% of the active ingredient.

The following examples, illustrating the invention, are not to be construed as being limitations thereon. Temperatures are given in degrees Centigrade and all parts wherever given are parts by weight.

Example 1

The mixture of 1 g of 8-chloro-4-dimethylaminomethylidene-1-phenyl-3,4-dihydro-2-benzazepin-5-one, 0.33 g of hydrazine hydrate and 45 ml of methanol is refluxed for 4 hours and evaporated under reduced pressure. The residue is taken up in the minimum amount of acetone-ethanol, the solution acidified with ethereal hydrogen chloride and the precipitate formed filtered off, to yield the 8-chloro-6-phenyl-1H,4H-pyrazolo[4,3-d](2)benzazepine dihydrochloride of the formula

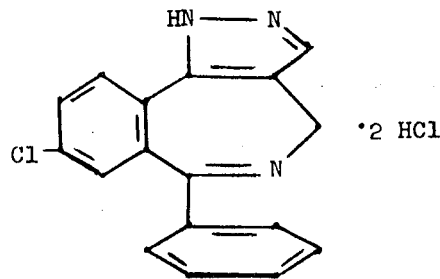

melting at 268° – 270°.

The starting material is prepared as follows: The mixture of 68 g of 5-chloro-2-methylbenzoic acid and 170 ml of thionyl chloride is refluxed for 1 hour, evaporated under reduced pressure and the residual acid chloride dried in a high vacuum. It is taken up in 500 ml of benzene and the solution added dropwise to the suspension of 100 g of anhydrous aluminum chloride and 600 ml of benzene while stirring and cooling with an ice bath. Thereupon the bath is removed and the mixture stirred at room temperature for 16 hours. It is combined with some ice, followed by 340 ml of 2N hydrochloric acid and the mixture stirred for a half hour. It is diluted with diethyl ether, the organic layer separated and washed with 5% sodium hydroxide and saturated aqueous sodium chloride, dried and evaporated under reduced pressure, to yield the 5-chloro-2-methylbenzophenone showing in the I.R. spectrum a strong band at 1660 cm⁻¹.

The mixture of 116 g thereof, 2.2 liters of benzene, 5 g of p-toluenesulfonic acid and 120 ml of ethyleneglycol is refluxed on a water separator for 48 hours. Thereupon additional 3 g of p-toluenesulfonic acid are added and refluxing continued for 40 hours. After cooling the mixture in an ice bath, it is washed with ice cold aqueous sodium carbonate, dried, evaporated and the residue crystallized from n-hexane, to yield the corresponding ethylene ketal melting at 76°–77°.

The mixture of 18 g thereof (dried in a high vacuum), 700 ml of carbon tetrachloride, 12.3 g of N-bromosuccinimide and a few crystals of 2,2'-azobis-(2-methylpropionitrile) is refluxed until all of the N-bromosuccinimide has disappeared. It is cooled, filtered and the filtrate evaporated under reduced pressure. The residue is immediately taken up in 1.1 liters of ice cold methanol and 23.5 ml of thiophenol, immediately followed by 225 ml of N methanolic sodium hydroxide. The mixture is stirred for 20 hours at room temperature, cooled in an ice bath and the precipitate (A) formed filtered off. The filtrate is evaporated under reduced pressure, the residue taken up in diethyl ether, the mixture washed with cold 2N aqueous sodium hydroxide, dried and evaporated. This residue and (A) are combined and crystallized from methanol, to yield the 5-chloro-2-phenylmercaptomethyl-benzophenone ethylene ketal melting at 89°–91°.

To the solution of 51.8 g thereof in 610 ml of dry tetrahydrofuran, 101 ml of 1.6 molar n-butyl lithium in hexane are added while stirring under nitrogen at −67° to −70°. After one hour 400 ml of 6 molar ethyleneoxide in tetrahydrofuran are added during five minutes, the temperature allowed to rise to −35° and the mixture stirred for two hours at room temperature. It is evaporated under reduced pressure, the residue taken up in 400 ml of dioxane, 400 ml of 2N hydrochloric acid are added and the mixture refluxed for one hour. It is concentrated under reduced pressure to about half its volume, the concentrate extracted with methylene chloride, the extract dried and evaporated, to yield the 5-chloro-2-(3-hydroxy-1-phenylmercaptopropyl)-benzophenone, showing in the NMR spectrum a quartet at $\theta = 4.65$ ppm.

To the mixture of 58.2 g thereof, 28 ml of N,N-diisopropylethylamine and 700 ml of diethyl ether, 21.6 ml of methanesulfonyl chloride are added dropwise while stirring at 0°. After 16 hours the mixture is washed with ice cold 5% hydrochloric acid, ice water and ice cold aqueous carbonate, dried and evaporated under reduced pressure and below 30°. The residual methanesulfonate is taken up to 700 ml of methanol, saturated with ammonia, while stirring and after two hours the solution is again saturated with ammonia. It is allowed to stand at room temperature for 14 days, the precipitate (B) formed filtered off and the filtrate evaporated. The residue is taken up in diethyl ether, the solution extracted with 2N sulfuric acid, the aqueous solution made basic with 30% aqueous sodium hydroxide and extracted with methylene chloride. The extract is dried, evaporated, the residue combined with (B) and recrystallized from methanol, to yield the 8-chloro-1-phenyl-5-phenylmercapto-3,4-dihydro-2-benzazepine melting at 118°–119°.

The solution of 10 g thereof in 100 ml of methylene chloride is neutralized with 5.6 ml of 5.4N ethereal hydrogen chloride and evaporated. The residue is taken up in 100 ml of methylene chloride and 83 ml of molar triethyloxonium tetrafluoroborate in methylene chloride are added while stirring under nitrogen. After 24 hours the mixture is evaporated under reduced pressure, the residue dissolved in 160 ml of dimethylsulfoxide and the solution stirred under nitrogen at 50° for 6 hours. It is evaporated under reduced pressure, the residue taken up in diethyl ether, the solution washed with water and extracted with 5% hydrochloric acid. The pH of the acidic solution is adjusted to 8 with sodium carbonate and the mixture extracted with diethyl ether. The extract is washed with water and saturated aqueous sodium chloride, the washings re-extracted with diethyl ether, the combined extracts dried and evaporated. The residue is taken up in the minimum amount of acetone, the solution neutralized with methanesulfonic acid in acetone and the precipitate formed filtered off, to yield the 8-chloro-1-phenyl-3,4-dihydro-2-benzazepin-5-one methanesulfonate melting at 185°–186°.

It is taken up in water, the solution made basic with aqueous sodium carbonate and extracted with diethyl ether. The extract is dried and evaporated, to yield the corresponding free base.

The mixture of 2.2 g of 8-chloro-1-phenyl-3,4-dihydro-2-benzazepin-5-one and 15 ml of dimethylformamide-dimethylacetal is refluxed for one hour and the excessive reagent removed under reduced pressure at a temperature not exceeding 135°. The residue is crystallized from diethyl ether, to yield the 8-chloro-4-dimethylaminomethylidene-1-phenyl-3,4-dihydro-2-benzazepin-5-one; m.p. 179°–180°.

EXAMPLE 2

The solution of 1.74 g of 8-chloro-6-(2-fluorophenyl)-10a-hydroxy-1-methyl-3a,10a-dihydro-1H,4H-pyrazolo[4,3-d](2)-benzazepine in 60 ml of chloroform is stirred with 100 ml of 0.1 N hydrochloric acid for 15 minutes, the pH of the aqueous phase adjusted to 8 with aqueous sodium carbonate and the mixture again stirred for 5 minutes. The organic layer is separated, dried, evaporated and the residue recrystallized from diethyl ether-hexane, to yield the 8-chloro-6-(2-fluorophenyl)-1-methyl-1H,4H-pyrazolo-[4,3-d](2)benzazepine melting at 128°–130°. The corresponding dihydrochloride melts at 190° with decomposition.

The starting material is prepared as follows: The solution of 141 g of α,p-dichlorotoluene in 200 ml of tetrahydrofuran is added dropwise to an ice-cold saturated solution of dimethylamine in 1 liter of tetrahydrofuran and the mixture stirred for 2 days at 25°. It is diluted with diethyl ether, washed with 2N aqueous sodium hydroxide, the organic layer dried, evaporated, the residue distilled and the fraction boiling at 106°/12 mm Hg collected, to yield the N,N-dimethyl-4-chlorobenzylamine.

To the solution of 81.6 g thereof in 1.5 lt of diethyl ether 360 ml of 1.6 molar n-butyl lithium in hexane are added dropwise while stirring at 0°–5° under nitrogen. After 3 hours the solution of 58 g of 2-fluorobenzonitrile in 1.5 lt of diethyl ether is added dropwise while stirring, the mixture refluxed for 3 hours and stirred at room temperature for 16 hours. Thereupon crushed ice and 265 ml of 5N hydrochloric acid are added, the mixture refluxed for ½ hour, cooled and the aqueous layer separated. It is made basic with 30% aqueous sodium hydroxide, extracted with methylene chloride, the extract dried, evaporated and the residue dried in a high vacuum at 100°, to yield the 3-chloro-2'-fluoro-6-dimethylaminomethyl-benzophenone melting at 91°–92°.

To the solution of 138 g thereof in 3.2 lt of methylene chloride, that of 55 g of cyanogen bromide in 300 ml of methylene chloride is added dropwise while stirring and cooling with ice. After stirring overnight, the mixture is evaporated under reduced pressure at 40°. The residue is taken up in 2.4 lt of methanol 56.8 ml of thiophenol are added, followed by 596 ml of N methanolic sodium hydroxide, the mixture stirred for 2 hours at 0° and overnight at room temperature. It is cooled again, filtered and the residue washed with methanol, to yield the 3-chloro-2'-fluoro-6-phenylmercaptomethyl-benzophenone melting at 81°–82°.

The mixture of 144.6 g thereof, 386 g of p-toluenesulfonic acid, 800 ml of ethylene glycol and 3 lt of benzene is refluxed at the water separator for 19 days and evaporated under reduced pressure, to yield the corresponding ethylene ketal melting at 69°.

Said ketal is further processed analogous to the method shown for the 5-chloro-2-phenylmercaptomethyl-benzophenone ethylene ketal in the previous example, to yield the 8-chloro-1-(2-fluoro-phenyl)-4-dimethylaminomethylidene-3,4-dihydro-2-benzazepin-5-one melting at 224°. (The analogously prepared 2-chlorophenyl- compound melts at 207°).

2 g thereof are added to the solution of 0.7 g of methylhydrazine in 100 ml of ethanol, the mixture refluxed for 45 minutes and evaporated under reduced pressure. The residue is recrystallized from ethyl acetate-hexane, to yield the 8-chloro-6-(2-fluorophenyl)-10a-hydroxy-1-methyl-3a,10a-dihydro-1H,4H-pyrazolo[4,3-d](2) benzazepine melting at 114°–115°.

EXAMPLE 3

The mixture of 0.72 g of 8-chloro-1-(2-chlorophenyl)-4-dimethylaminomethylidene-3,4-dihydro-2-benzazepin-5-one, 0.64 g of benzylhydrazine and 35 ml of ethanol is refluxed for 45 minutes and evaporated under reduced pressure. The residue is taken up in 20 ml methylene chloride, the solution washed with aqueous sodium bicarbonate and stirred with 6 ml of N hydrochloric acid for 20 minutes. The aqueous solution is made basic with sodium carbonate, the mixture stirred, the organic layer separated, dried and evaporated. The residue is taken up in the minimum amount of ethanol, the solution acidified with ethereal hydrogen chloride and the precipitate formed filtered off, to yield the 1-benzyl-8-chloro-6-(2-chlorophenyl)-1H,4H-pyrazolo[4,3-d](2)benzazepine hydrochloride melting at 218°–221°.

EXAMPLE 4

To the solution of 3.3 g of 8-chloro-6-(2-chlorophenyl)-1H,4H-pyrazolo-[4,3-d](2)benzazepine and 50 ml of dimethylformamide, 0.72 g of 57% sodium hydride in mineral oil (washed three times with diethyl ether) are added and the mixture stirred for 30 minutes. Thereupon 1.45 g of methyl iodide in 10 ml of toluene are added and the mixture stirred at room temperature for 16 hours. It is diluted with diethyl ether, washed with water, dried and evaporated. The residue is chromatographed on silica gel and the column eluted with chloroform, to yield a faster moving fraction, yielding after evaporation, the 8-chloro-6-(2-chlorophenyl)-2-methyl-2H,4H-pyrazolo[4,3-d](2)benzazepine of the formula

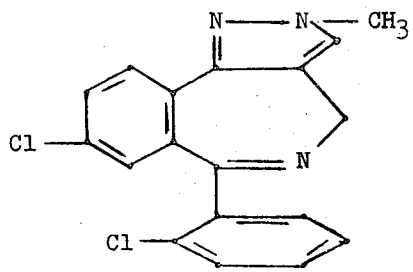

melting at 160°–161°, and a slower moving fraction, yielding the corresponding 1-methyl-isomer, the hydrochloride of which melts at 209°–211°.

EXAMPLE 5

The mixture of 0.33 g of 8-chloro-6-(2-chlorophenyl)-1H,4H-pyrazolo[4,3-d](2)benzazepine, 0.141 g of ethyl chloroformate, 0.16 g of pyridine and 10 ml of methylene chloride is stirred at room temperature for 2 hours. It is diluted with chloroform, washed with aqueous sodium bicarbonate, the organic phase separated, dried and evaporated. The residue is taken up in the minimum amount of acetone and the solution neutralized with ethereal hydrogen chloride, to yield the 8-chloro-6-(2-chlorophenyl)-2-ethoxycarbonyl-2H,4H-pyrazolo[4,3-d](2)benzazepine hydrochloride melting at 151°–152°.

EXAMPLE 6

To the solution of 0.33 g of 8-chloro-6-(2-chlorophenyl) 1H,4H-pyrazolo[4,3-d](2)benzazepine in 10 ml of methylene chloride, the mixture of 0.16 g of dimethylcarbamoyl chloride and 0.15 g of pyridine is added and the whole stirred for 2 hours at room temperature. The mixture is diluted with methylene chloride, washed with ice-cold aqueous sodium carbonate, dried and evaporated under reduced pressure. The residue is chromatographed on silica gel and eluted with benzene-methanol(95:5), to yield the 8-chloro-6-(2-chlorophenyl)-2-dimethylcarbamoyl-2H,4H-pyrazolo[4,3-d](2)benzazepine melting at 175°–176°.

EXAMPLE 7

The solution of 1.45 g of 8-chloro-6-(2-fluorophenyl)-1H,4H-pyrazolo[4,3-d](2)benzazepine and 1.4 ml of methylisocyanate in 20 ml of tetrahydrofuran is refluxed for 5 hours under nitrogen and evaporated under reduced pressure. The residue is taken up in chloroform, the solution filtered through a column of 15 g of silica gel, the first fractions collected, evaporated and the residue recrystallized from diethyl ether, to yield the 8-chloro-6-(2-fluorophenyl)-2-methylcarbamoyl-2H,4H-pyrazolo[4,3-d](2)benzazepine melting at 192°–193°.

EXAMPLE 8

The suspension of 0.5 g of 3-chloro-6-(1-methyl-4-aminomethyl-5-pyrazolyl)-2'-fluorobenzophenone monophosphate in 20 ml of 0.5N aqueous sodium hydroxide and 50 ml of methylene chloride is shaken for 5 min., the organic layer separated, dried and evaporated, to yield the 8-chloro-6-(2-fluorophenyl)-1-methyl-1H,4H-pyrazolo[4,3-d](2)benzazepine melting at 128°; it is identical with that obtained according to Example 2.

The starting material is obtained as follows: The solution of 10 g of 3-chloro-2'-fluoro-6-phenylmercaptomethyl-benzophenone ethylene ketal (Example 2) in 50 ml of methyl iodide is refluxed under nitrogen for 5 days. It is evaporated and the formed methyl phenyl thioether distilled off at 60°/0.1 mm Hg, to yield the 3-chloro-2'-fluoro-6-iodomethyl-benzophenone ethylene ketal.

The mixture of 9.6 g thereof, 5 g of sodium bicarbonate and 50 ml of dimethylsulfoxide is stirred for 20 minutes at 110°, cooled and poured onto ice. The mixture is extracted with diethyl ether, the extract washed with water and saturated aqueous sodium chloride, dried, evaporated and the residue recrystallized from diethyl ether-hexane, to yield the 3-chloro-2'-fluoro-6-formylbenzophenone ethylene ketal melting at 103°–105°.

To the solution of 1.6 g thereof in 60 ml of diethyl ether, 3 ml of 2.3 molar methyl lithium in diethyl ether are added while stirring and cooling with ice. After 5 minutes 20 ml of water are added cautiously, the organic layer separated, washed with saturated aqueous sodium chloride, dried and evaporated, to yield the 3-chloro-2'-fluoro-6-(1-hydroxy-ethyl)-benzophenone ethylene ketal showing in the NMR-spectrum a doublet at $\theta=1.1$ ppm (in deuterochloroform).

To the solution of 1.8 g thereof in 100 ml of diethyl ether, 25 ml of the solution (obtained from 100 g of sodium dichromate dihydrate, 300 ml of water, 136 ml of concentrated sulfuric acid and diluting it with water to 500 ml) are added while stirring. After 40 minutes the mixture is poured on ice, the organic phase separated and washed with aqueous sodium bisulfite, water, aqueous sodium bicarbonate and saturated aqueous sodium chloride. It is dried and evaporated, to yield the 6-acetyl-3-chloro-2'-fluorobenzophenone ethylene ketal showing in the NMR spectrum a singlet at $\theta=2.4$ ppm.

The mixture of 1.1 g thereof and 7 ml of dimethyl formamide dimethylacetal is refluxed for 16 hours and evaporated under reduced pressure, to yield the 3-chloro-6-(3-dimethylaminoacryloyl)-2'-fluoro-benzophenone ethylene ketal showing in the NMR-spectrum a broad singlet at $\theta=2.7$ ppm.

The mixture of 1.3 g thereof, 0.3 g of methylhydrazine and 25 ml of ethanol is refluxed for 7 hours under nitrogen and evaporated. The residue is chromatographed on silica gel and the column eluted first with benzene, then diethyl ether and the ether eluate collected, to yield the 3-chloro-2'-fluoro-6-(1-methyl-5-pyrazolyl)-benzophenone ethylene ketal showing in the NMR-spectrum a singlet at $\theta=3.1$ and a doublet at $\theta=5.95$ ppm.

The solution of 650 mg thereof in 2.7 ml of ethylene dichloride is added dropwise to the complex, prepared from 265 mg of dimethylformamide and 555 mg of phosphorous oxychloride, while cooling with ice, and dissolved in 1.8 ml of ethylene dichloride, while stirring and the mixture is refluxed for 2 hours under nitrogen. After cooling the solution of 2.45 g of sodium acetate trihydrate in 3.6 ml of water is added and the mixture refluxed for 15 minutes. It is diluted with methylene chloride and water, the organic layer separated and dried, to yield the 3-chloro-2'-fluoro- 6-(1methyl-4-formyl5-pyrazolyl)-benzophenone ethylene ketal, showing in the NMR-spectrum a band at $\theta=9.13$ ppm.

The mixture of 660 mg thereof, 3 ml of pyridine and 170 mg of O - methyl-hydroxylamine hydrochloride is stirred for 16 hours at room temperature and evaporated under reduced pressure. The residue is taken up in chloroform and the solution filtered through a short column of silica gel, to yield the corresponding methoxime.

The mixture of 130 mg thereof, 25 ml of diethyl ether and 100 mg of lithium alluminum hydride is stirred at room temperature for 16 hours. Thereupon 0.1 ml of water, 0.1 ml of 15% aqueous sodium hydroxide and 0.3 ml of water are added, the mixture filtered and the filtrate extracted with N hydrochloric acid. The acidic layer is separated, made basic with 2N aqueous sodium hydroxide, extracted with methylene chloride, the extract dried and evaporated, to yield the 3-chloro-6-(1-methyl-4-aminomethyl-5-pyrazolyl)-2'-fluorobenzophenone ethylene ketal, showing in the NMR-spectrum a singlet at $\theta=3.03$ and a triplet at $\theta=8.0$ ppm.

The mixture of 100 mg thereof, 10 ml of dioxane and 10 ml of 2N hydrochloric acid is refluxed for 1 hour under nitrogen and the dioxane evaporated. The aqueous solution is cooled, admixed to methylene chloride, made basic with 2N aqueous sodium hydroxide and extracted with diethyl ether. The extract is dried, filtered into the solution of 50 mg of phosphoric acid in 1 ml of ethanol and the precipitate filtered off, to yield the 3-chloro-6-(1-methyl-4-aminomethyl-5-pyrazolyl)-2'-fluorobenzophenone monophosphate melting at 180°.

EXAMPLE 9

To the solution of 2 g of 8-chloro-6-(2-fluorophenyl)-1-methyl-1H,4H-pyrazolo [4,3-d](2)benzazepine in 120 ml of ethanol and 2.2 ml of 3.7N ethereal hydrogen chloride, 1.1 g of sodium cyanoborohydride are added and the mixture stirred at room temperature for 45 minutes while keeping the pH thereof between 4 and 6 by adding more ethereal hydrogen chloride. It is evaporated under reduced pressure, the residue take up in methylene chloride, the solution washed with ice-water and aqueous sodium carbonate, dried and evaporated. The residue is taken up in ethanol, the solution neutralized with ethereal hydrogen chloride and the precipitate collected, to yield the 5,6-dihydro-derivative of said starting compound.

The mixture of 2g thereof, 5.5 ml of formic acid and 5.5 ml of 37% aqueous formaldehyde is refluxed for 2 hours, poured onto ice and made basic with aqueous sodium hydroxide to pH=11. The mixture is extracted with methylene chloride, the extract dried, evaporated and the residue taken up in acetone. The solution is neutralized with ethereal hydrogen chloride and the precipitate collected, to yield the 8-chloro-6-(2-fluorophenyl)-1,5-dimethyl-5,6-dihydro-1H,4H-pyrazolo [4,3-d](2)benzazepine hydrochloride melting at 270°.

EXAMPLE 10

According to the methods illustrated by the previous examples, the following compounds of Formulae III and IV are prepared from equivalent amounts of the corresponding starting materials: $R_6 = Cl$, $R_3 = H$

| No. | $R_4$ | $R_5$ | $R_7$ | Salt | m.p.°C |
|---|---|---|---|---|---|
| 1 | H | H | — | $CH_3SO_3H$ | 221 |
| 2 | $CH_3$ | H | — | 2HCl | 255 |
| 3 | H | F | — | " | 225(dec.) |
| 4 | n—$C_3H_7$ | F | — | " | 199 |
| 5 | H | Cl | — | HCl | 220(dec.) |
| 6 | $(CH_2)_2N(C_2H_5)_2$ | F | — | cyclamate | 105 " |
| 7 | $(CH_2)_2N(C_2H_5)_2$ | Cl | — | 2 HCl | 195(dec.) |
| 8 | $(CH_2)_2OH$ | F | — | HCl | 169 |
| 9 | $(CH_2)_3N(C_2H_5)_2$ | F | — | cyclamate | 110(dec.) |
| 10 | — | F | $CH_3$ | — | 139 |
| 11 | — | F | $CO_2C_2H_5$ | HCl | 168 |
| 12 | — | Cl | $CONH—CH_3$ | — | 192 |
| 13 | — | F | $CON(CH_3)_2$ | — | 170 |
| 14 | — | Cl | $CSNH—CH_3$ | — | 195 |

EXAMPLE 11

Preparation of 10,000 tablets each containing 25 mg of the active ingredient:

Formula:
| | |
|---|---:|
| 8-chloro-6-(2-fluorophenyl)-1-methyl-1H,4H-pyrazolo-[4,3-d](2)benzazepine dihydrochloride | 250.00 g |
| Lactose | 1,956.00 g |
| Corn starch | 90.00 g |
| Polyethylene glycol 6,000 | 90.00 g |
| Talcum powder | 90.00 g |
| Magnesium stearate | 24.00 g |
| Purified water | q.s |

Procedure:

All the powders are passed through a screen with openings of 0.6 mm. Then the drug substance, lactose, talcum, magnesium stearate and half of the starch are mixed in a suitable mixer. The other half of the starch is suspended in 45 ml of water and the suspension added to the boiling solution of the polyethylene glycol in 180 ml of water. The paste formed is added to the powders which are granulated, if necessary, with an additional amount of water. The granulate is dried overnight at 35°, broken on a screen with 1.2 mm openings and compressed into tablets using concave punches with 7.1 mm diameter, uppers bisected.

Preparation of 10,000 capsules each containing 10 mg of the active ingredient:

Formula:
| | |
|---|---:|
| 8-chloro-6-(2-fluorophenyl)-1-methyl-1H,4H-pyrazolo-[4,3-d](2)benzazepine | 500.0 g |
| Lactose | 2,350.0 g |
| Talcum powder | 150.0 g |

Procedure:

All the powders are passed through a screen with openings of 0.6 mm. Then the drug substance is placed in a suitable mixer and mixed first with the talcum, then with the lactose until homogenous. No. 2 capsules are filled with 300 mg of the mixture, using a capsule filling machine.

EXAMPLE 12

The mixture of 450 mg of 3,2'-dichloro-6-(1-t. butyl-4-formyl-3-pyrazolyl)-benzophenone, 400 mg of anhydrous sodium sulfate and 10 ml of saturated methanolic ammonia is stirred at room temperature for 3 days. It is evaporated, the residue taken up in methylene chloride, the solution washed with aqueous sodium bicarbonate, dried and evaporated, to yield the 8-chloro-6-(2-chlorophenyl-4-hydroxy-2-t. butyl- 2H,4H-pyrazolo[4,3-d](2)benzazepine, showing the NMR-spectrum bands at $\theta$=4.92 and 1.44 ppm.

The starting material is prepared as follows: To the solution of 17 g of potassium t-butoxide in 150 ml of ethyleneglycol, 24 g of 4-chlorophenyl propargylketone are added portionwise while stirring at 0°. After one hour 9 g of acetic acid are added, the mixture poured onto ice, diluted with diethyl ether and the pH thereof adjusted to 8 with sodium bicarbonate. The ethereal layer is separated, washed with saturated aqueous sodium chloride, dried and evaporated, to yield the 2-(4-chlorobenzoyl)-acetaldehyde ethylene acetal.

The mixture of 11.9 g thereof, 11.73 g of pyridinium chloride, 8.97 g of t. butylhydrazine and 76 ml of pyridine is stirred at 80° for 23 hours and evaporated under reduced pressure. The residue is taken up in methylene chloride the solution washed with aqueous sodium bicarbonate, dried, evaporated and the residue recrystallized from hot hexane, to yield the 1-t. butyl-3-(4-chlorophenyl)-pyrazole melting at 62°.

The solution of 700 mg thereof in 25 ml of diethyl ether and 2.2 ml of 1.6 molar n-butyl lithium in hexane is stirred at 0° for one hour. Thereupon the solution of 480 mg of 2-chlorobenzonitrile in 10 ml of diethyl ether is added and the mixture stirred for 5½ hours at room temperature. It is diluted with 30 ml of water, extracted with diethyl ether, the extract washed with saturated aqueous sodium chloride and evaporated under reduced pressure. The residue is taken up in 20 ml of methanol and 5 ml of N hydrochloric acid, the solution refluxed for two hours concentrated, the concentrate diluted with methylene chloride and neutralized with sodium carbonate. The organic layer is separated, dried, concentrated and the precipitate collected, to yield the 3,2'-dichloro-6-(1-t. butyl-3-pyrazolyl)-benzophenone, melting at 105°–107°.

To the solution of 370 mg thereof in 1.5 ml of ethylene chloride, that of the complex, obtained from 146 mg of dimethylformamide and 306 mg of phosphorus oxychloride at 0°, in 1 ml of ethylene chloride is added and the mixture refluxed for 2 hours. Thereupon the solution os 1.35 g of sodium acetate trihydrate in 2 ml of water is added, refluxing continued for 15 minutes, the mixture cooled and diluted with methylene chloride and water. The organic layer is separated, dried and evaporated, to yield the 3,2'-dichloro-6-(1-t. butyl-4-formyl-3-pyrazolyl)-benzophenone, showing the NMR-spectrum bands at $\delta$=9.63, 7.95 and 1.95 ppm.

EXAMPLE 13

According to the analogous method described in the previous examples, the following compounds of Formula XI are prepared from equivalent amounts of the corresponding starting materials:

a. 4-dimethylaminomethyldiene-1-phenyl-3,4-dihydro-2-benzazepin-5-one, m.p. 134°–136° (methanesulfonate m.p. 185°–187°);

b. 8-chloro-4-dimethylaminomethylidene-1-(2-fluoro or chlorophenyl)-3,4-dihydro-2-benzazepin-5-one, melting at 224° or 207° respectively.

Other compounds XI can be prepared as follows: The mixture of 1.9 g of 8-chloro-4-hydroxymethylidene-1-phenyl-3,4-dihydro-2-benzazepin-5-one, 30 ml of ethanol and 0.7 g of morpholine is stirred for 16 hours at room temperature and evaporated under reduced pressure. The residue is crystallized from diethyl ether, to yield the c. 8-chloro-4-morpholinomethylidene-1-phenyl-3,4-dihydro-2-benzazepin-5-one, m.p. 144°–146°;

The starting material is prepared as follows: To the solution of 2.6 g of 8-chloro-1-phenyl-3,4-dihydro-2-benzazepin-5-one in 4 ml of diethyl ether, 0.5 g of sodium hydride in 10 ml of diethyl ether are added and the mixture stirred for ½ hour. Thereupon 1.2 ml of ethyl formate and 0.1 ml of ethanol are added and the mixture refluxed for 24 hours. It is cooled in an ice bath, 30 ml of water are added, the aqueous layer separated, acidified with 2N hydrochloric acid and the precipitate formed filtered off, to yield the 8-chloro-4-hydroxymethylidene-1-phenyl-3,4-dihydro-2-benzazepin-5-one hydrochloride melting at 185° with decomposition.

It can also be obtained by hydrolyzing 2.1 g of the 8-chloro-4-dimethylaminomethylidene-1-phenyl-3,4-dihydro-2-benzazepin-5-one with 5 ml of 2N hydrochloric acid at 25° for 2 hours while stirring. The precipitate formed is filtered off to yield said hydrochloride melting at 185° with decomposition. It is taken up in water, the pH of the solution adjusted to 7.5 with aqueous sodium carbonate, extracted with methylene chloride, the extract dried and evaporated, to yield said starting material melting at 131°–132°.

In the analogous manner these other compounds are prepared.

d. 8-chloro-4-(methylamino- or 3-hydroxy-propylamino)-methylidene-1-phenyl-3,4-dihydro-2-benzazepin-5-one, melting at 176° and 205° (dec.) respectively;

e. 8-chloro-4-methylaminomethylidene-1-(2-fluoro- or 2-chloro-phenyl)-3,4-dihydro-2-benzazepin-5-one hydrochloride, melting at 225° and 210° (dec.) respectively.

Tablets or capsules of these compounds are prepared analogous to Example 11.

I claim:

1. An antianxiety and antidepressant pharmaceutical composition comprising an anxiolytic or antidepressively effective amount of a compound of the formulae

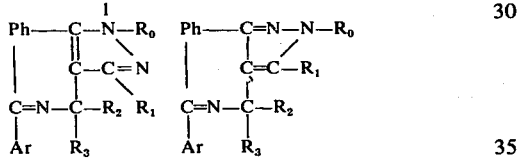

wherein Ar is unsubstituted phenyl or phenyl substituted by one or two, of the same or different substituents selected from the group consisting of lower alkyl, lower alkoxy, halo or trifluoromethyl, Ph is 1,2-phenylene substituted by one or two halogen atoms, $R_o$ is hydrogen, lower alkyl, (hydroxy, lower alkoxy or Am)-$C_mH_{2m}$ or AR-$C_nH_{2n}$, wherein Am is amino, mono- or di-lower alkylamino, lower alkyleneimino or mono-aza-, oxa- or thia-alkyleneimino, wherein the additional nitrogen, oxygen or sulfur atom is separated from the imino-nitrogen by at least 2 carbon atoms, $m$ is an integer from 1 to 7, $n$ such from 0 to 7, each of $R_1$ and $R_2$ is hydrogen or lower alkyl, and $R_3$ is hydrogen, lower alkyl, hydroxy or lower alkanoyloxy, or a 5,6-dihydro- or 5-lower alkyl-5,6-dihydro derivative, an N-oxide of the compounds containing no hydrogen attached to nitrogen, or a lower alkanoyl, alkoxycarbonyl, AmCO, AmCS or cyano derivative of the compounds containing at least one hydrogen attached to nitrogen, or a therapeutically useful acid addition salt thereof, together with an enterally or parenterally applicable pharmaceutical excipient.

2. A composition as claimed in claim 1, wherein the effective compound corresponds to the formulae

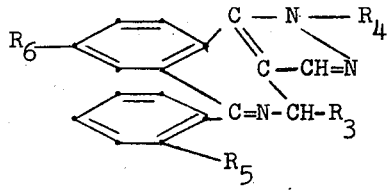

or

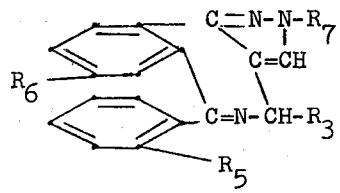

wherein $R_3$ is hydrogen or hydroxy, $R_4$ is hydrogen, methyl, ethyl, n- or i-propyl, n-, i- or t-butyl, 2- or 3-(hydroxy, dimethylamino- or diethylemino)-(ethyl or propyl) or benzyl, each of $R_5$ and $R_6$ is fluoro or chloro and $R_7$ is $R_4$ or formyl, acetyl, (methoxy or ethoxy)-carbonyl, mono- or dimethyl or -ethyl-carbamoyl or -thiocarbamoyl, or a therapeutically acceptable acid addition salt thereof.

3. A composition as claimed in claim 1, wherein the effective compound is the 8-chloro-6-(2-fluorophenyl)-1-methyl-1H,4H-pyrazolo[4,3-d]-(2)benzazepine, or a therapeutically useful acid addition salt thereof.

* * * * *